United States Patent
Pugh et al.

(10) Patent No.: US 9,804,416 B2
(45) Date of Patent: Oct. 31, 2017

(54) ENERGIZABLE OPHTHALMIC LENS WITH AN EVENT-BASED COLORATION SYSTEM

(71) Applicant: Johnson & Johnson Vision Care, Inc., Jacksonville, FL (US)

(72) Inventors: Randall B. Pugh, Jacksonville, FL (US); Karson S. Putt, Jacksonville, FL (US); Camille Higham, Jacksonville, FL (US); Sharika Snook, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1049 days.

(21) Appl. No.: 13/899,510

(22) Filed: May 21, 2013

(65) Prior Publication Data
US 2014/0350372 A1   Nov. 27, 2014

(51) Int. Cl.
*G02C 7/04*       (2006.01)
*A61B 5/145*      (2006.01)
(Continued)

(52) U.S. Cl.
CPC ............ *G02C 7/046* (2013.01); *A61B 3/101* (2013.01); *A61B 5/14507* (2013.01);
(Continued)

(58) Field of Classification Search
CPC ............ A61B 5/14532; A61B 5/14539; A61B 5/14507; A61B 5/14546; G02C 11/10;
(Continued)

(56) References Cited

U.S. PATENT DOCUMENTS

| | | | | |
|---|---|---|---|---|
| 7,931,832 B2 * | 4/2011 | Pugh | ................ | B29D 11/00125 264/1.32 |
| 2009/0244477 A1 * | 10/2009 | Pugh | ................ | B29D 11/00125 351/158 |

(Continued)

FOREIGN PATENT DOCUMENTS

| | | | |
|---|---|---|---|
| EP | 2508935 A1 | 10/2012 | |
| WO | WO 0025662 A1 | 5/2000 | |

(Continued)

OTHER PUBLICATIONS

PCT International Search Report PCT/US2814/838734 dated Oct. 2, 2014.

*Primary Examiner* — Meredith Weare (57) ABSTRACT

The present invention provides a device for an energizable Ophthalmic Lens with an event coloration mechanism. The event coloration mechanism may color or change color based on some predefined event. For example, a predefined constituent or predefined condition of the tear fluid may be indicative of the predefined event, and the event coloration mechanisms may interact with the tear fluid, accordingly. The event coloration mechanism may provide the energizable functionality of the Ophthalmic Lens in some embodiments. In others, the event coloration mechanism may be passive but may interact and interface with the electrical components of the Ophthalmic Lens, such as, for example, those included within the Media Insert. Event coloration mechanisms may be combined with additional functionalities that may be included in an energizable Ophthalmic Lens.

21 Claims, 5 Drawing Sheets

(51) Int. Cl.
  *G02C 7/08* (2006.01)
  *G02C 11/00* (2006.01)
  *A61B 3/10* (2006.01)
  *G02C 7/02* (2006.01)
  *A61B 5/00* (2006.01)

(52) U.S. Cl.
  CPC ...... *A61B 5/14532* (2013.01); *A61B 5/14539* (2013.01); *G02C 7/021* (2013.01); *G02C 7/04* (2013.01); *G02C 7/083* (2013.01); *G02C 11/10* (2013.01); *A61B 5/14546* (2013.01); *A61B 5/6821* (2013.01); *A61B 5/7445* (2013.01)

(58) Field of Classification Search
  CPC .......... G02C 7/083; G02C 7/046; G02C 7/04; G02C 7/021
  See application file for complete search history.

(56) References Cited

U.S. PATENT DOCUMENTS

2010/0113901 A1* 5/2010 Zhang ................ A61B 5/14532
  600/319
2012/0259188 A1* 10/2012 Besling .............. A61B 5/14507
  600/319

FOREIGN PATENT DOCUMENTS

| WO | WO 02067688 A1 | 9/2002 |
| WO | WO 2011010267 A1 | 1/2011 |
| WO | WO 2013049000 A1 | 4/2013 |

\* cited by examiner

ENERGIZABLE OPHTHALMIC LENS WITH AN EVENT-BASED COLORATION SYSTEM

FIELD OF USE

This invention describes methods, apparatus and devices related to energizable Ophthalmic Lenses with an event coloration mechanism, wherein the event coloration mechanism may provide a visual indication upon the occurrence of a predefined event.

BACKGROUND

Traditionally, an Ophthalmic Device, such as a contact lens, an intraocular lens, or a punctal plug included a biocompatible device with a corrective, cosmetic, or therapeutic quality. A contact lens, for example, can provide one or more of vision correcting functionality, cosmetic enhancement, and therapeutic effects. Each function is provided by a physical characteristic of the lens. A design incorporating a refractive quality into a lens can provide a vision corrective function. A pigment incorporated into the lens can provide a cosmetic enhancement. An active agent incorporated into a lens can provide a therapeutic functionality. Such physical characteristics may be accomplished without the lens entering into an energized state.

More recently, active components have been included in a contact Lens, and the inclusion may involve the incorporation of energizing elements within the Ophthalmic Device. The relatively complicated components to accomplish this effect may derive improved characteristics by including them in insert devices which are then included with standard or similar materials useful in the fabrication of state of the art Ophthalmic Lenses.

The functionality of the Ophthalmic Lens may not be limited to ophthalmic functions. When placed on an eye, an Ophthalmic Lens is in contact with the ocular environment, such as, tear fluid, which may include constituents similar to those contained in blood. Accordingly, an Ophthalmic Lens may provide a platform to monitor specific attributes of the ocular environment, such as tear fluid constituents. More specifically, color indicators may be included in energizable Ophthalmic Lenses.

It may be desirable to improve the process, methods, and resulting devices for realizing event coloration mechanisms of various kinds. It may be anticipated that some of the solutions for event coloration mechanisms in energizable Ophthalmic Lenses may provide novel aspects for non-energized devices and other biomedical devices. Accordingly novel methods, devices, and apparatus relating to event coloration mechanisms in an Ophthalmic Lens are therefore important.

SUMMARY

Accordingly, the present invention includes innovations relating to an Ophthalmic Lens with a Media Insert with an event coloration mechanism. The Ophthalmic Lens may comprise a soft lens portion, wherein the soft lens portion comprises a polymerized Reactive Monomer Mixture; an event coloration mechanism, wherein the event coloration mechanism is capable of providing a visual indication in the Ophthalmic Lens based on an occurrence of a predefined event; and the Media Insert, wherein the hydrogel lens is in contact with at least a portion of the Media Insert and a portion of the event coloration mechanism.

In some embodiments, the event coloration mechanism may be located within the Media Insert. The Media Insert may comprise a power source located within the Media Insert; a processor in electrical communication with the power source; conductive traces capable of allowing electrical communication between the processor and the power source; and an energizable element in electrical communication with the processor and the power source, wherein the energizable element is capable of providing functionality to the Ophthalmic Lens.

In other such embodiments, the event coloration mechanism may comprise a power source; a coloration portion; conductive traces capable of activating the coloration portion by electrically connecting the power source and the coloration portion; and a tube portion in circuit with the conductive traces, power source, and coloration portion, wherein the tube portion comprises a body and an Encapsulant layer, wherein the Encapsulant layer is capable of surrounding the body, and wherein the tube portion is capable of limiting an activation of the coloration portion.

In some embodiments, the coloration portion may comprise a liquid crystal, wherein the liquid crystal is capable of a Resting Orientation and a first Energized Orientation, and wherein the liquid crystal in the Resting Orientation comprises a first color and the liquid crystal in the first Energized Orientation comprises a second color.

In other embodiments, the body may comprise a reactive material capable of reacting with a specified tear fluid constituent, wherein the tear fluid constituent is capable of permeating the Encapsulant layer. The predefined event may include, for example, a pathogen level, a biomarker level, or an active agent level in the tear fluid.

In some embodiments, the event coloration mechanism may be in electrical communication with the power source and the processor, the event coloration mechanism comprising a network of optical fibers; and an illuminating device in electrical communication with the power source and the processor, wherein the illuminating device is capable of illuminating the network of optical fibers. The network of optical fibers may be arranged in a sunburst design, and the network of optical fibers may comprise a portion within the optic zone, wherein the portion within the optic zone is visible to the wearer.

In some other embodiments, the event coloration mechanism may further comprise a first resistance tab in electrical communication with the processor, wherein the first resistance tab is capable of binding the tear fluid constituent, wherein the binding is capable of increasing a resistance of the first resistance tab; and the processor further comprises an executable software capable of controlling the illuminating device based on the resistance. The predefined constituent may comprise, for example, a pathogen, a biomarker, or an active agent.

Alternatively, the predefined event may comprise a condition of a component located within the Media Insert. In such embodiments, the event coloration mechanism may comprise a reservoir comprising a colored substance; and an Encapsulant layer capable of encapsulating the reservoir, wherein the predefined condition is capable of degrading the Encapsulant layer. In some exemplary embodiments, the component may comprise the power source, and the condition may comprise a leeching of a caustic substance from a pre-designated area for the power source. Similarly, the predefined event may comprise a predefined pH level within the Media Insert.

Such embodiments of an event coloration mechanism may be combined with other functionalities of an energizable Ophthalmic Lens. For example, the energizable element may comprise a variable optic portion, wherein an energization of the variable optic portion is capable of altering a power of the Ophthalmic Lens.

DETAILED DESCRIPTION OF THE INVENTION

The present invention describes an energizable Ophthalmic Lens device with an event coloration mechanism. In general, according to some embodiments of the present invention, event coloration mechanisms may be incorporated with an energizable Ophthalmic Lens, such as those that include a Media Insert. The event coloration mechanisms may be passive or energizable and may interface or interact with an ocular environment. This proximity with the ocular environment may allow for a wide range of events. Alternatively, the event coloration mechanism may interact or interface with the Media Insert, which may alert the wearer of the condition of the Media Insert.

In some embodiments, the event may be a specific or threshold concentration of a biomarker within the tear fluid. Monitoring the concentration of certain biomarkers within tear fluid may allow a patient or doctor to develop a more effective therapy schedule, such as with light therapy and melatonin levels. Alternatively, the coloration may be able to alert the patient of ineffective or dangerous levels of the biomarker, which may be high levels or low levels, depending on the biomarker. For example, high levels of glucose in a diabetic patient may require an emergency response.

An alternative example of an event may be medication levels in the tear fluid. Some medications are most effective within a specific concentration range, and some may even be dangerous at concentrations above that range. Such medications may include, for example, those that treat mental disorders, thyroid diseases, or degenerative brain diseases, such as, Alzheimer's disease.

For example, valproic acid is a common medication that may treat epilepsy or bipolar, in lower doses. Frequent blood tests may be required to monitor the concentration of the medication to ensure the concentration is within the therapeutic range and not into the toxic range, which may cause, for example, renal failure or increase in symptoms of the mental disorder. A constant monitoring system may allow a patient to maintain safe and effective levels.

Other events may include the presence or concentration of specific pathogens, for example, those that may cause ocular infections or may be indicative of non-ocular infections or diseases, such as keratitis, conjunctivitis, corneal ulcers, and cellulitis. Such pathogens may include, for example, *Acanthamoeba keratitis, Pseudomona aeruginosa, Neisseria gonorrhoeae,* and *Staphylococcus* and *Streptococcus* strains, such as *S. aureus*.

In the following sections, detailed descriptions of embodiments of the invention will be given. The description of both preferred and alternative embodiments are exemplary embodiments only, and it is understood that to those skilled in the art that variations, modifications, and alterations may be apparent. It is therefore to be understood that said exemplary embodiments do not limit the scope of the underlying invention.

Glossary

In this description and claims directed to the presented invention, various terms may be used for which the following definitions will apply:

Back Curve Piece or Back Insert Piece: as used herein refers to a solid element of a multi-piece Rigid Insert which when assembled into the said insert will occupy a location on the side of the lens that is on the back. In an Ophthalmic Device, said piece would be located on the side of the insert that would be closer to the user's eye surface. In some embodiments, the back curve piece may contain and include a region in the center of an Ophthalmic Device through which light may proceed into the user's eye, which may be called an Optic Zone. In other embodiments, the piece may take an annular shape where it does not contain or include some or all of the regions in an optic zone. In some embodiments of an ophthalmic insert, there may be multiple back curve pieces and one of them may include the optic zone, while others may be annular or portions of an annulus.

Component: as used herein refers to a device capable of drawing electrical current from an Energy Source to perform one or more of a change of logical state or physical state.

Encapsulate: as used herein refers to creating a barrier to separate an entity, such as, for example, a Media Insert, from an environment adjacent to the entity.

Encapsulant: as used herein refers to a layer formed surrounding an entity, such as, for example, a Media Insert, that creates a barrier to separate the entity from an environment adjacent to the entity. For example, Encapsulants may be comprised of silicone hydrogels, such as Etafilcon, Galyfilcon, Narafilcon, and Senofilcon, or other hydrogel contact lens material. In some embodiments, an Encapsulant may be semipermeable to contain specified substances within the entity and preventing specified substances, such as, for example, water, from entering the entity.

Energized: as used herein refers to the state of being able to supply electrical current to or to have electrical energy stored within.

Energized Orientation: as used herein refers to the orientation of the molecules of a Liquid Crystal when influenced by an effect of a potential field powered by an Energy Source. For example, a device containing Liquid Crystals may have one Energized Orientation if the Energy Source operates as either on or off. In other embodiments, the Energized Orientation may change along a scale affected by the amount of Energy applied.

Energy: as used herein refers to the capacity of a physical system to do work. Many uses within this invention may relate to the said capacity being able to perform electrical actions in doing work.

Energy Source: as used herein refers to device capable of supplying Energy or placing a biomedical device in an Energized state.

Energy Harvesters: as used herein refers to device capable of extracting energy from the environment and convert it to electrical energy.

Event: as used herein refers to a defined set of parameters, such as, for example, a biomarker level, energization level, pH level, or a visual recognition of a particular object. An event may be specific to a wearer, such as a level of medication, or may be generally applicable to all wearers, such as temperature.

Front Curve Piece or Front Insert Piece: as used herein refers to a solid element of a multi-piece Rigid Insert which when assembled into the said insert will occupy a location on the side of the lens that is on the front. In an Ophthalmic Device, a Front Curve Piece would be located on the side of the insert that would be further from the user's eye surface. In some embodiments, the piece may contain and include a region in the center of an Ophthalmic Device through which light may proceed into the user's eye, which may be called an Optic Zone. In other embodiments, the piece may take an annular shape where it does not contain or include some or all of the regions in an optic zone. In some embodiments of an ophthalmic insert, there may be multiple front curve pieces and one of them may include the optic zone, while others may be annular or portions of an annulus.

Lens-forming mixture or Reactive Mixture or Reactive Monomer Mixture (RMM): as used herein refers to a monomer or prepolymer material that can be cured and cross-linked or cross-linked to form an Ophthalmic Lens. Various embodiments can include lens-forming mixtures with one or more additives such as UV blockers, tints, photoinitiators or catalysts, and other additives one might desire in an Ophthalmic Lenses such as, contact or intraocular lenses.

Lens-forming Surface: as used herein refers to a surface that is used to mold a lens. In some embodiments, any such surface can have an optical quality surface finish, which indicates that it is sufficiently smooth and formed so that a lens surface fashioned by the polymerization of a lens forming material in contact with the molding surface is optically acceptable. Further, in some embodiments, the lens-forming surface can have a geometry that is necessary to impart to the lens surface the desired optical characteristics, including without limitation, spherical, aspherical and cylinder power, wave front aberration correction, corneal topography correction and the like as well as any combinations thereof.

Liquid Crystal: as used herein refers to a state of matter having properties between a conventional liquid and a solid crystal. A Liquid Crystal cannot be characterized as a solid but its molecules exhibit some degree of alignment. As used herein, a Liquid Crystal is not limited to a particular phase or structure, but a Liquid Crystal may have a specific resting orientation. The orientation and phases of a Liquid Crystal may be manipulated by external forces such as, for example, temperature, magnetism, or electricity, depending on the class of Liquid Crystal.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized Ophthalmic Device. The energization elements and circuitry may be embedded in the Media Insert. The Media Insert defines the primary purpose of the energized Ophthalmic Device. For example, in embodiments where the energized Ophthalmic Device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose or administering medicine.

Mold: as used herein refers to a rigid or semi-rigid object that may be used to form lenses from uncured formulations. Some preferred molds include two mold parts forming a front curve Mold part and a back curve Mold part.

Ophthalmic Lens or Ophthalmic Device or Lens: as used herein refers to any device that resides in or on the eye, in contrast to spectacle lenses. The device may provide optical correction, may be cosmetic, or provide some functionality unrelated to optic quality. For example, the term Lens may refer to a contact Lens, intraocular Lens, overlay Lens, ocular insert, optical insert, or other similar device through which vision is corrected or modified, or through which eye physiology is cosmetically enhanced (e.g. iris color) without impeding vision. Alternatively, Lens may refer to a device that may be placed on the eye with a function other than vision correction, such as, for example, monitoring of a constituent of tear fluid or means of administering an active agent. In some embodiments, the preferred Lenses of the invention may be soft contact Lenses that are made from silicone elastomers or hydrogels, which may include, for example, silicone hydrogels and fluorohydrogels.

Optic Zone: as used herein refers to an area of an Ophthalmic Lens through which a wearer of the Ophthalmic Lens sees.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate for a specified, reestablished time period.

Reenergize or Recharge: as used herein refers to a restoration to a state with higher capacity to do work. Many uses within this invention may relate to restoring a device to the capability to flow electrical current at a certain rate for a specified, reestablished time period.

Released from a mold: as used herein refers to a lens is either completely separated from the mold, or is only loosely attached so that it can be removed with mild agitation or pushed off with a swab.

Resting Orientation: as used herein refers to the orientation of the molecules of a Liquid Crystal device in its resting, non-energized state.

Rigid Insert: as used herein refers to an insert that maintains a predefined topography and includes a greater modulus than a hydrogel in contact with all or part of the Rigid Insert. When included in a Contact Lens, the Rigid Insert may contribute to the functionality of the Lens. For example, varying topography of or densities within the Rigid Insert may define zones, which may correct vision in users with astigmatism.

Stabilizing Feature: as used herein refers to a physical characteristic that stabilizes an Ophthalmic Device to a specific orientation on the eye, when the Ophthalmic Device is placed on the eye. In some embodiments, the Stabilizing Feature may add sufficient mass to ballast the Ophthalmic Device. In some embodiments, the Stabilizing Feature may alter the front curve surface, wherein the eyelid may catch the Stabilizing Feature and the user may reorient the Lens by blinking. Such embodiments may be enhanced by including Stabilizing Features that may add mass. In some exemplary embodiments, Stabilizing Features may be a separate material from the encapsulating biocompatible material, may be an insert formed separately from the molding process, or may be included in the Rigid Insert or Media Insert.

Stacked Integrated Component Devices or SIC Devices: as used herein refers to the product of packaging technologies that can assemble thin layers of substrates, which may contain electrical and electromechanical devices, into operative integrated devices by means of stacking at least a portion of each layer upon each other. The layers may comprise component devices of various types, materials, shapes, and sizes. Furthermore, the layers may be made of various device production technologies to fit and assume various contours.

Three-dimensional Surface or Three-dimensional Substrate: as used herein refers to any surface or substrate that has been three-dimensionally formed where the topography is designed for a specific purpose, in contrast to a planar surface.

Ophthalmic Lens with an Event Coloration Mechanism

Active Event Coloration Mechanisms

Proceeding to FIGS. 1A-1E, an Ophthalmic Lens 140 with an event coloration mechanism 101-105 is illustrated. In some embodiments, the event coloration mechanism 101-105 may be contained within a Media Insert 100. The Media Insert 100 with the event coloration mechanism 101-105 may include a power source 106, wherein the power source 106 may provide the energization to the event coloration mechanism 101-105. In some such embodiments, the event that affects the event coloration mechanism may be a change in an energization level. In some embodiments, the power source 106 may comprise a tab.

The event coloration mechanism 101-105 may comprise a coloration band 104 that may be sensitive to different energization levels. For example, the coloration band 104 may comprise organic light emitting diodes or liquid crystal, which may have a Resting Orientation color and an Energized Orientation color. In some such embodiments, the liquid crystal may be capable of multiple Energized Orientations, which may allow for multiple colorations on a single coloration band 104. Alternatively, the coloration band 104 may comprise multiple layers or multiple bands, which may allow for a broader spectrum of coloration.

The Media Insert 100 may also comprise a processor 102 that may be in electrical communication with a sensor 103. The sensor 103 may comprise an antenna that may be able to receive information wirelessly from an external device, such as a triggering mechanism or a Smartphone. Alternatively, the sensor 103 may be capable of detecting blink times or patterns, which may allow a wearer to control the activation through deliberate blinking.

The processor 102 may be able to receive data transmitted from the sensor 103 and may activate and adjust the energization level accordingly. The energization level may be controlled through an activation circuit 105, which may prevent or limit the amount of power transferred to the coloration band, directly or indirectly through the conductive material 101 in contact with the coloration band 104.

In some embodiments, the Media Insert 100 with the coloration band 104 may further include a limbic ring (not shown) or an iris pattern 147, which may provide a static and natural background or foreground to the coloration band 104. The iris pattern 147 may be included with the Media Insert 100 through a variety of processes, such as, for example, printing on a surface of the Media Insert 100. The Media Insert 100 may be encapsulated within an Ophthalmic Lens 140. The Media Insert 100 may be annular so that the portion of the Media Insert 100 that would be in the Optic Zone may be void of material. Such an annular shape may be particularly appropriate where the Media Insert 100 does not provide an optical functionality, such as vision correcting.

In embodiments where the coloration band may activate at different levels of power, such as with a liquid crystal, the iris pattern may be tinted with varying colors. For example, in an Ophthalmic Lens 140 with a Media Insert 100, the coloration band may provide a base, inactive color 147. The coloration band may be energized to a first level 150, second level 160, and a third level 170.

Figure 1A:
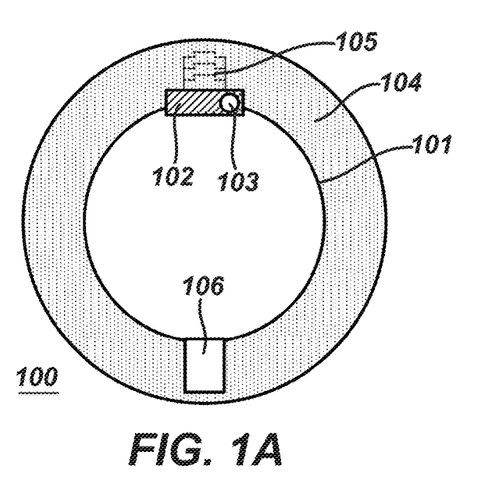
FIGS. 1A-1E illustrate an exemplary embodiment of an energizable event coloration mechanism for inclusion in an Ophthalmic Lens.
Figure 1B:
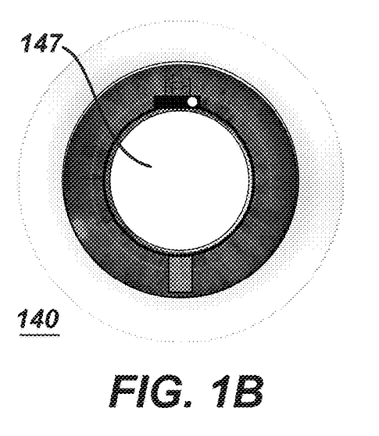
Figure 1C:
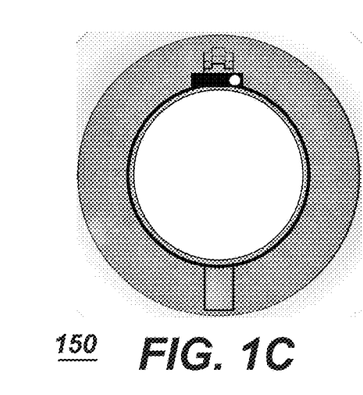
Figure 1D:
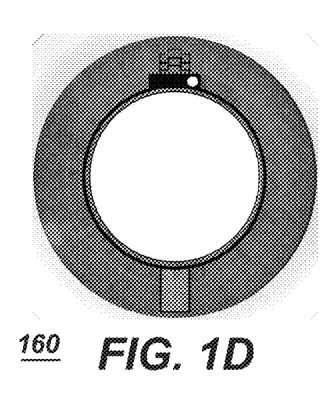
Figure 1E:
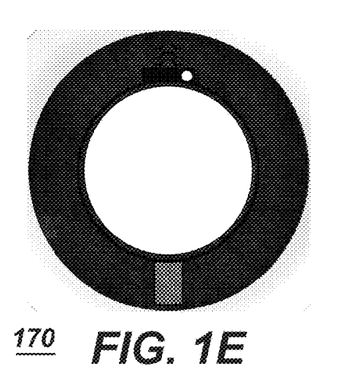
Figure 2A:
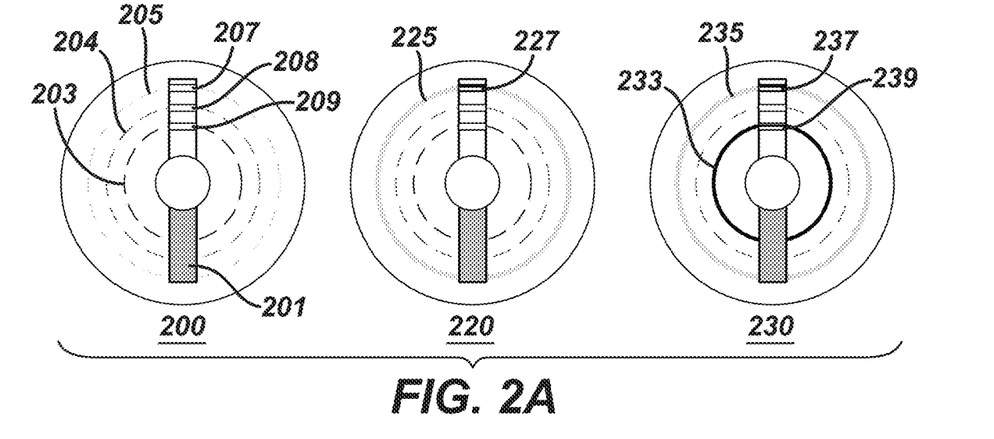
FIGS. 2A-2C illustrate an alternate embodiment of an energizable event coloration mechanism for inclusion in an Ophthalmic Lens.
Figure 2B:
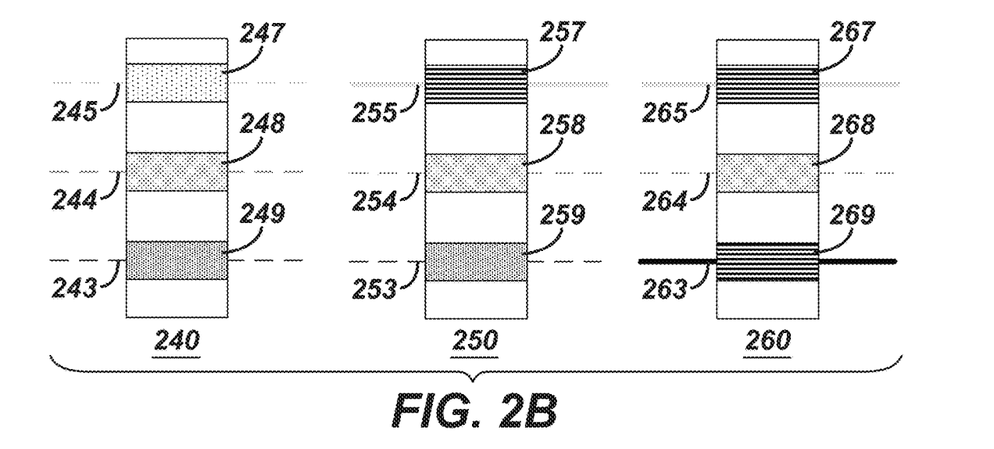
Figure 2C:
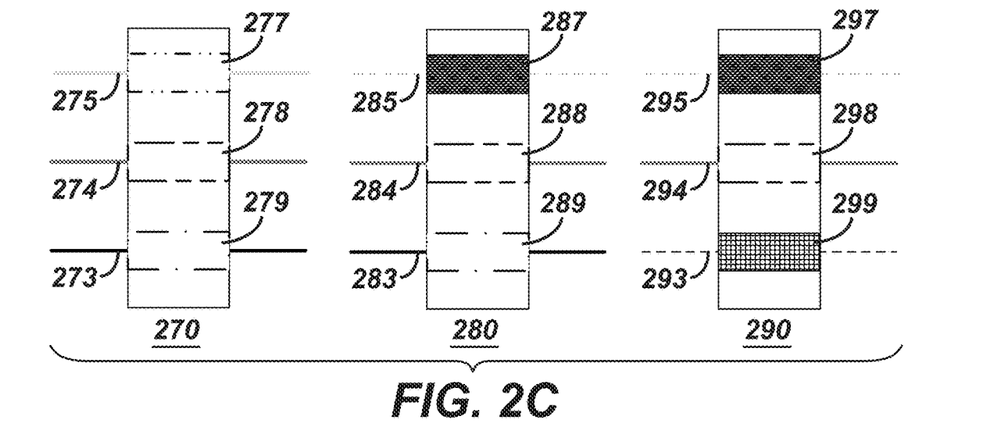

Proceeding to FIGS. 2A-2C, alternate embodiments of a Media Insert with an event coloration mechanism are illustrated. FIG. 2A illustrates a Media Insert 200 with an event coloration mechanism comprising a tube portion 207-209 where an event may occur and coloration rings 203-205 in electrical communication with the power source 201. The coloration rings may comprise a conductive material or may be in contact with a conductive material. For example, the coloration rings 203-205 may comprise liquid crystal wherein activation may shift the liquid crystal from a Resting Orientation to an Energized Orientation, thereby changing the color of the liquid crystal.

In some embodiments, the tube portion 207-209 may comprise multiple tubes, wherein each tube may indicate a separate and independent event. In some such embodiments, the occurrence of an event in a first tube 209 may not affect the other tubes 207, 208. For example, in a Media Insert 220 with three tube portions 227-229, an event may occur in the outer tube 227 that may allow the outer ring 225 to activate, but may not affect the other tubes 228, 229 or rings 223, 224. As another example of a partially activated Media Insert 230, one event may occur in the outer tube 237 activating the outer ring 235, and a separate event may occur in the inner tube 239 activating the inner ring 233.

When inactive, the tube portion 207-209 may inhibit the circulation of energy from the power source to the coloration rings 203-205. The activating event may allow sufficient energy to activate the coloration ring 203-205, for example, by causing the tube portion to increase in conductivity. In some embodiments, the activation may occur along a scale of energization, for example, with a brighter coloration at higher levels of activation. Alternatively, the tube portion may function by increasing resistivity when an event occurs, thereby deactivating the coloration ring 203-205.

Proceeding to FIG. 2B, an exemplary embodiment of reactive tube portions 240, 250, 260 are illustrated. In some embodiments, an inactive Media Insert may comprise a set of three reactive tubes 247-249, wherein each reactive tube 247-249 contains, for example, a substance, material, or mixture that may react with a specific molecule. The reaction may be indicative of the event specific to the individual tube 247-249. Where the event relates to a concentration of some substance in the tear fluid, the reaction may occur directly with that substance or may occur with a separate substance that may indicate the concentration of the monitored substance.

For example, if the event is a threshold concentration of glucose in the tear fluid, the tube may contain the enzyme glucose oxidase. As the glucose concentration increases, the glucose oxidase may react with the glucose producing hydrogen peroxide, which may result in increased conductivity. Because other electroactive biological components may affect the conductivity within the tube, the tube may be lined with or comprise a selective barrier to minimize interference with non-glucose components. For example, the tube may be lined with Nafion. In addition to the glucose oxidase, other components may be included within the tube to increase the reactivity between the glucose oxidase and glucose within the tear fluid.

Alternatively, in embodiments that monitor the concentration of valproic acid, the tube may contain specific proteins that would be able to bind to the valproic acid up to a specific concentration. The non-binding valproic acid may be indicative of the effective quantities within the tear fluid. The conductivity within the tube may increase with the increased concentration of the acid.

Proceeding to FIG. 2C, an alternate embodiment of tube portions 270, 280, 290 are illustrated. In such embodiments, the tube portions 270, 280, 290 may function based on an accumulation of specific molecules. Unlike the reactive tubes illustrated in FIG. 2B that operate by increasing conductivity, an accumulation tube may function in an opposite manner by increasing resistivity. Therefore, an event may inhibit the circulation of energy, which may deactivate the coloration ring 285, 293, 295.

When the events have not occurred, the Media Insert may be completely active 270. In some such embodiments, the tube portions 277-279 may comprise a hollow, conductive material, which may attract or may be selectively permeable to specific tear fluid components, such as biomarkers or proteins. An increase in concentration of the specified component may cause an accumulation within the tube portions 277-279, thereby decreasing the conductivity of the tube. The material for the tube portions may be selected so that the change in resistivity occurs only at specific concentrations of the component.

Each tube portion may individually affected by a separate event. For example, in a partially deactivated Media Insert 280, 290, the outer tube 287 may deactivate the outer coloration ring 285, leaving the other coloration rings 284, 283 active if specific events have not occurred in the other tube portions 288, 289. Similarly, two coloration rings 295, 293 may be deactivated by separate events in their respective tube portions 297, 299, which may leave a third coloration ring 294 and tube portion 298 active.

Alternatively, not shown, the tube portions may comprise or contain a conductive substance or mixture, for example. The conductive substance or mixture may bind with a specific component to decrease in conductivity. Similar to embodiments where the tube portion 277-279 is hollow, the tube may comprise a material that is selectively permeable or attractive to the specific component.

In some embodiments, not shown, the tube portion may function by agglutination, such as through a coagulase test, wherein a higher concentration of the pathogen may adhere to a compound within the event coloration mechanism 702-706 and may cause clumping or the formation of precipitate. The precipitate may add resistance or may react with another compound in the event coloration mechanism 702-706 through a separate reaction. Alternatively, the event coloration mechanism 202-206 may comprise a reagent that changes conductivity upon reaction, such as with some oxidase tests.

In some embodiments, the tube portions may utilize a mixture of processes indicate a mix of events, which may be tailored according to a patient's needs. For example, each tube portion may indicate a different biomarker concentration, such as glucose, melatonin, and serotonin. An additional tube portion may allow for the monitoring of temperature, wherein the conductivity of the tube portion changes with body temperature.

Alternatively, the tube portions may indicate a series of event related to a single disorder. For example, one tube may increase conductivity with an increase in glucose levels, and another tube may decrease in conductivity when a diabetic medication is in low concentration. Such an embodiment may act as a reminder to the patient to take their medication or may allow the patient to eat accordingly. Another example may include monitoring serotonin levels in a first tube portion and depression medications in other tube portions. This may be particularly significant where a patient takes a combination of medications.

Some event coloration mechanisms may be reversible, such as when the wearer has effectively responded to the event. For example, after a wearer has rinsed the Ophthalmic Lens, the level of pathogens or protein may be sufficiently reduced to allow for safe use of the Ophthalmic Lens. Alternatively, the coloration may be reversible on the eye, such as where the event is a level of glucose and the wearer has effectively adjusted the level, such as, for example, by taking insulin.

Figure 3A:
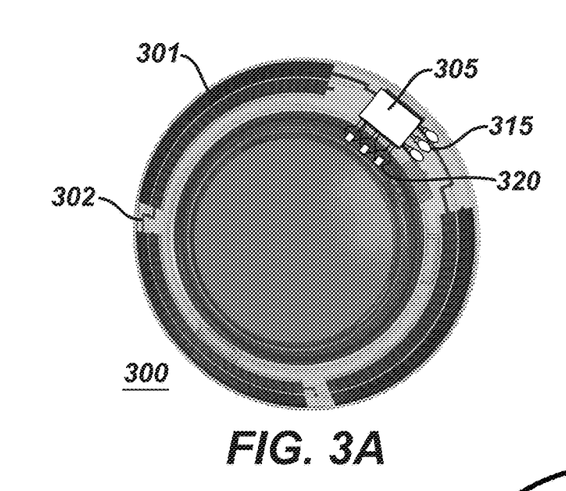
FIGS. 3A-3C illustrate an alternate embodiment of an energizable event coloration mechanism for inclusion in an Ophthalmic Lens.
Figure 3B:
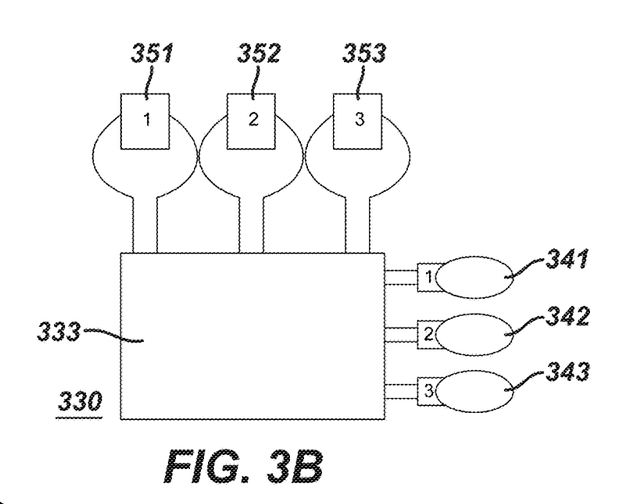
Figure 3C:
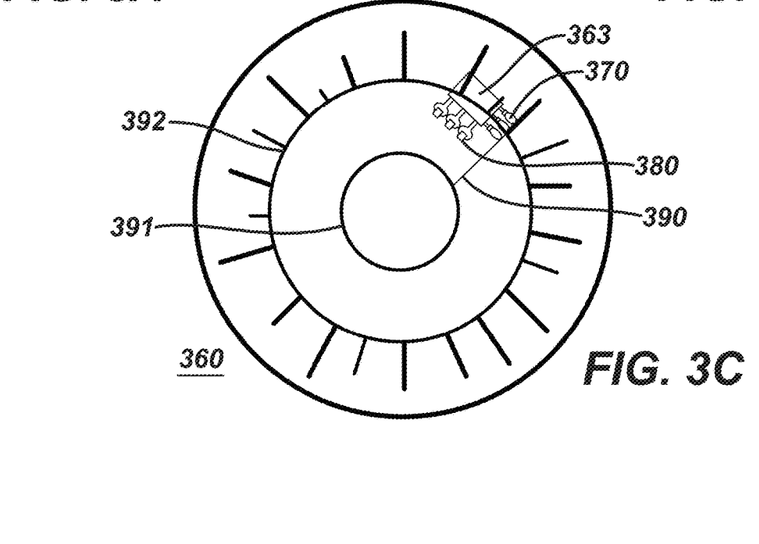

Proceeding to FIGS. 3A-3C, an alternative embodiment of a Media Insert 300 with an event coloration mechanism 360 is illustrated. The power source 301 in the Media Insert 300 in FIGS. 3A-3C differs from the embodiment of the power source 201 in the Media Insert in FIGS. 2A-2C, which illustrates a tabular power source. Both embodiments, in addition to other embodiments, may be applied to an event coloration mechanism and are well within the inventive art disclosed herein.

In some embodiments, the Media Insert 300 may include a processor 303 that may be in electrical communication with the power source 301 through conductive traces 302. The processor 303 may be in electrical communication with resistance tabs 320 and an illumination mechanism 310, which may comprise part of the event coloration mechanism. The processor 333, resistance tabs 351-353, and illumination mechanisms 341-343 are illustrated in a zoomed in view 330.

In some embodiments, each resistance tab 351-333 may include, for example through coating, layering, or encapsulation, a binding compound. This embodiment may be particularly significant where the event depends on a concentration of a component within the tear fluid, such as those discussed with FIGS. 2A-2C. The binding component may bind with a specific component that may be found within tear fluid. As the specific compound binds to surface of the resistance tab 351, the resistance may increase.

The processor may include executable software, which may allow the processor to trigger an activation of a corresponding illumination mechanism 341 when the resistance of the resistance tab 351 is above or below some threshold resistance, which may reflect a concentration of the binding component within the tear fluid. Alternatively, the binding component may be an indirect indication of the event. For example, the presence of some components may cause or prompt the presence of other components. Where the event components are not easily bound, a secondary indicator may be more practical to bind to the resistance tabs 351-353.

In some embodiments, the events may be individually programmed, which may allow for customized indications of concentration. Similar to the tube portions 207-209 illustrated in FIG. 2A, the selection of the binding compound on the resistance tabs 351-353 may also be tailored to the patient's needs. For exemplary purposes, the event coloration mechanisms are illustrated with three separate event indicators. However, it may be obvious to those skilled in the art that other quantities of events and event indicators may be practical.

In some embodiments, the event coloration mechanism 360 may further comprise optic fibers 390-392, which may be illuminated by the illumination mechanism 370. Some such embodiments may be configured so that the illumination mechanism 370 may direct the light onto a core optic fiber 390, which may guide the light onto the other optic fibers 391, 392.

For example, the core optic fiber 390 may direct the light into optic fibers 391 within the optic zone, periphery fiber optics 392 not immediately visible to the wearer, or both. Optic fibers 391 within the optic zone may be able to alert the wearer of a specific event without impeding vision, which may be particularly significant where the event may require immediate action. Periphery fiber optics 392 may not be visible to the wearer without the use of a reflective surface, such as a mirror. In some embodiments, the periphery fiber optics 392 may be arranged to appear less artificial, for example through a sunburst pattern that may more naturally integrate into the wearer's iris pattern than a simple ring pattern.

In some alternative embodiments, this combination of an illuminating source, such as a light emitting diode, and a network of optic fibers may be applied to a cosmetic function, including, for example, the embodiments described in FIG. 1. The activation may be controlled by the wearer, such as through blinking patterns or wireless communication with an external device.

Proceeding to FIGS. 4A-4E, a series of activation levels for an exemplary embodiment of a Media Insert with an event coloration mechanism is illustrated. Similar to the event coloration mechanism described in FIGS. 1A-1E, an event coloration mechanism that includes an illumination mechanism may appear more natural if integrated with a base pattern 402. As shown in cross section, a Media Insert 400 may include electrical components 411 in the periphery portion. Where the Media Insert 400 includes an illumination-based event coloration mechanism, optic fibers 405 may be arranged in a pattern, such as in a sunburst, to naturally integrate with a limbic ring pattern 402 in the foreground or background.

Figure 4A:
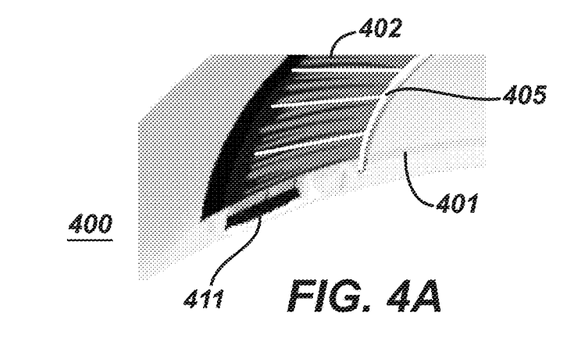
FIGS. 4A-4E illustrate an example of the alternate embodiment illustrated in FIGS. 3A-3C illustrate of an energizable event coloration mechanism for inclusion in an Ophthalmic Lens.
Figure 4B:
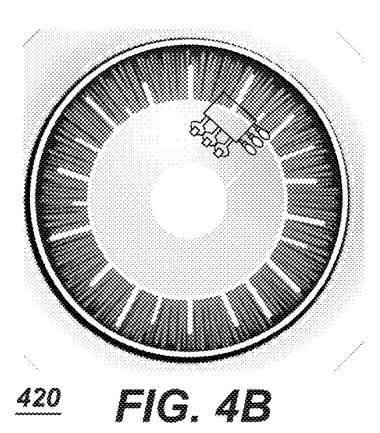

A completely inactive event coloration mechanism 420 may appear unlit. In some embodiments, the optic fiber may be tinted to define the inactive coloration. This may allow for a customizable coloration set. For example, the base color may be tinted to more closely match the wearer's natural eye color, and when activated, the illumination may appear more natural. Where the optic fiber may be tinted blue, a red light may appear violet and a yellow light may appear green. Alternatively, tinting may provide broader cosmetic choices.

Figure 4C:
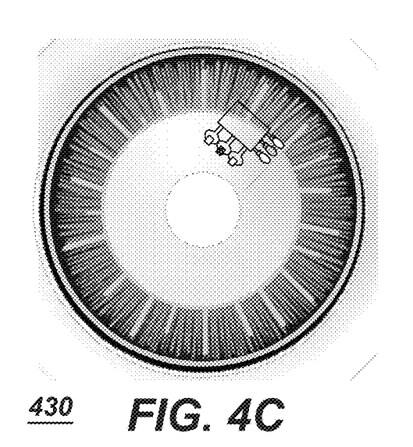
Figure 4D:
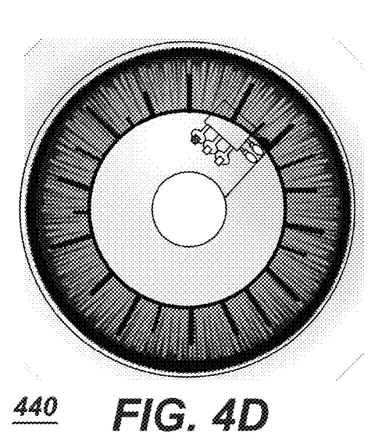

When the resistance on a resistance tab breaches a threshold level, the corresponding light may illuminate the optic fiber in the event coloration mechanism 430. Once the resistance returns to a level within a predetermined range, the light may turn off. In some embodiments, the predetermined range may include any resistance not included in the event range. A second resistance tab may breach a second threshold level independent to the first resistance tab, which may trigger a second light to illuminate the optic fiber in the event coloration mechanism 440.

Figure 4E:
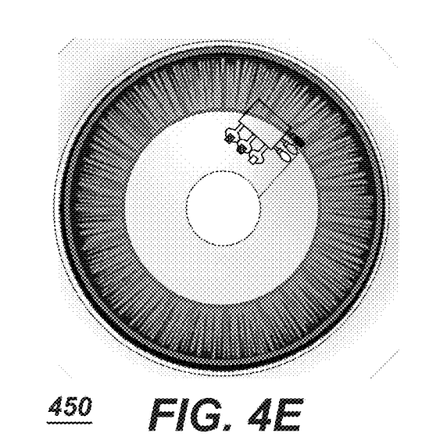
Figure 5A:
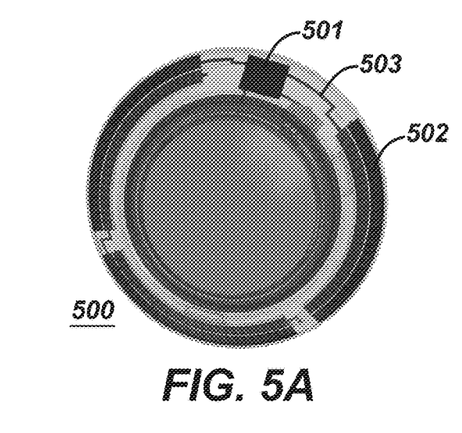
FIGS. 5A-5F illustrate an exemplary embodiment of a passive event coloration mechanism for inclusion in an energizable Ophthalmic Lens.
Figure 5B:
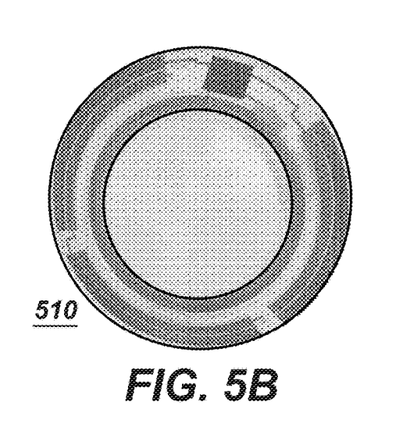
Figure 5C:
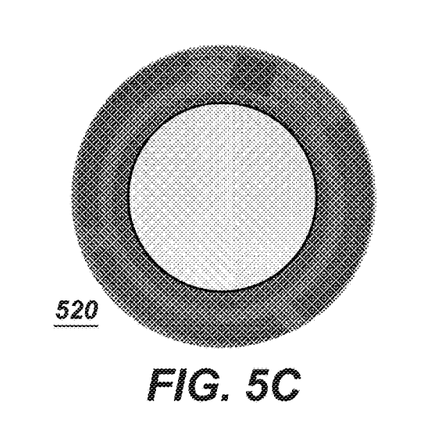
Figure 5D:
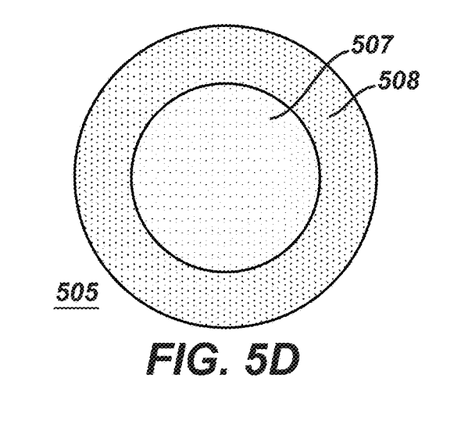
Figure 5E:
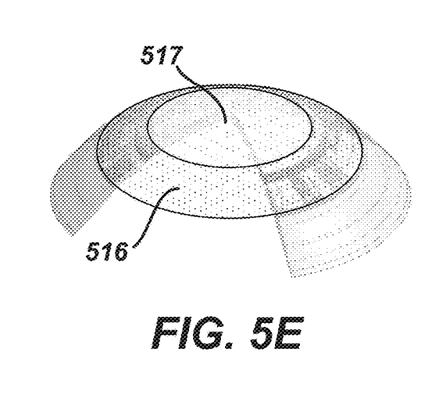
Figure 5F:
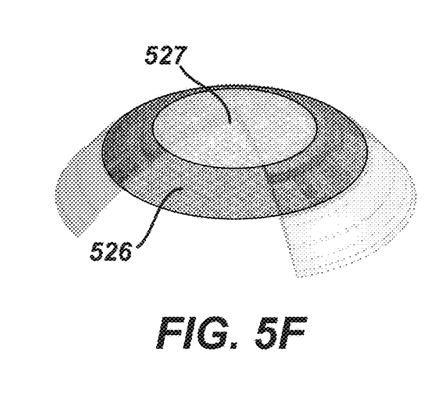

In some embodiments, multiple events may occur simultaneously, which may trigger the activation of multiple lights in the event coloration mechanism 450. In some such embodiments, the combination of lights may result in a distinct color, which would make the separate events apparent without requiring separate optic fibers for each event. For example, one event may trigger a blue light, and a separate event may trigger a yellow light. When the events occur simultaneously, the optic fibers may appear green. Such an embodiment, may not limit the coloration event mechanism to a single event notification.

Non-energizable Event Coloration Mechanisms

Proceeding to FIGS. 5A-5F, an example of a Media Insert 500 with a non-energizable event coloration mechanism is illustrated. In some embodiments, an event coloration mechanism may be included in an Ophthalmic Lens with a Media Insert but may not require energization. Similar to those embodiments in FIG. 5, the event coloration mechanism may be "activated" without requiring a power source. Embodiments described in FIGS. 5A-5F may also be incorporated in a Media Insert.

The event coloration mechanism 505 may comprise a periphery portion 506 that may visible to non-wearers in view of the Ophthalmic Lens. In some embodiments, particularly in those where the event may prompt emergency action from the wearer, the event coloration mechanism 505 may include an optic zone portion 507, which may be visible by the wearer.

In some embodiments, the event may relate to a condition of the Media Insert. The event coloration mechanism may function similarly to a litmus test, wherein the event coloration mechanism activates based on the pH within the Media Insert. For example, the event may be leakage from the active components, such as the battery, or the variable optic portion.

Alternatively, the event coloration mechanism may comprise a reservoir that may contain a colored substance, such as, for example, a dye. Prior to activation, the reservoir may not be visible. In some embodiments, the reservoir may be encapsulated with a degradable material, which may be irreversibly degraded by some compound in the Media Insert. For example, an electric component of the Media Insert may release a byproduct over time or during activation, and that byproduct may degrade the Encapsulant. Once degraded, the colored substance may be released into the Media Insert or into a second reservoir. Such an embodiment may indicate when a disposable Ophthalmic Lens should be disposed, for example, based on a manufacturer's recommended parameters.

Upon the occurrence of the event, the coloration may be immediately visible to the wearer and to non-wearers in view of the Ophthalmic Lens. The optic zone portion of the event coloration mechanism 527 may notify the wearer of the event without impeding vision. For example, the optic zone portion 527 may not be opaque but may add a tint to the wearer's vision. This may allow the wearer to quickly remove the Ophthalmic Lens before a leak may damage the eye.

Materials for Insert Based Ophthalmic Lenses

In some embodiments, a lens type can be a lens that includes a silicone-containing component. A "silicone-containing component" is one that contains at least one [—Si—O—] unit in a monomer, macromer, or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some embodiments, the Ophthalmic Lens skirt, which sometimes may be called an insert encapsulating layer, that surrounds the insert may be comprised of standard hydrogel lens formulations. Exemplary materials with characteristics that may provide an acceptable match to numerous insert materials may include the Narafilcon family; including Narafilcon A and Narafilcon B. Alternatively, the Etafilcon family; including Etafilcon A may represent good exemplary material choices. A more technically inclusive discussion follows on the nature of materials consistent with the art herein; but it may be clear that any material that may form an acceptable enclosure or partial enclosure of the sealed and encapsulated inserts are consistent and included.

Suitable silicone containing components include compounds of Formula I where:

$R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl (meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment, b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment, b is 5 to 400 or from 10 to 300, both terminal $R^1$ comprise monovalent reactive groups and the remaining $R^1$ are independently selected from monovalent alkyl groups having 1 to 18 carbon atoms that may have ether linkages between carbon atoms and may further comprise halogen.

In one embodiment, where a silicone hydrogel lens is desired, the lens of the present invention will be made from a Reactive Mixture comprising at least about 20 and preferably between about 20 and 70% wt silicone containing components based on total weight of reactive monomer components from which the polymer is made.

In another embodiment, one to four $R^1$ comprises a vinyl carbonate or carbamate of the formula:

wherein: Y denotes O—, S— or NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris (trimethylsiloxy)silane]; 3-[tris (trimethylsiloxy)silyl]propyl allyl carbamate; 3-[tris (trimethylsiloxy)silyl]propyl vinyl carbamate; trimethylsilylethyl vinyl carbonate; trimethylsilylmethyl vinyl carbonate, and Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

(*D*A*D*G)$_a$*D*D*E$^1$;

E(*D*G*D*A)$_a$*D*G*D*E$^1$ or;

E(*D*A*D*G)$_a$*D*A*D*E$^1$  Formulae IV-VI wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$a$ is at least 1;

A denotes a divalent polymeric radical of formula:

Formula VII

$R^{11}$ independently denotes an alkyl or fluoro-substituted alkyl group having 1 to 10 carbon atoms that may contain ether linkages between carbon atoms; y is at least 1; and p provides a moiety weight of 400 to 10,000; each of E and E$^1$ independently denotes a polymerizable unsaturated organic radical represented by formula:

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

Formula IX wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula X

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkages and crosslinkable monomers containing polyether and polysiloxanyl groups. Any of the foregoing polysiloxanes can also be used as the silicone-containing component in this invention.

Conclusion

The present invention, as described above and as further defined by the claims below, provides an event coloration mechanism for inclusion in an Ophthalmic Lens with a Media Insert. The event coloration mechanism may color or change color based on some predefined event. For example, a predefined constituent or predefined condition of the tear fluid may be indicative of the predefined event, and the event coloration mechanisms may interact with the tear fluid, accordingly.

The event coloration mechanism may provide the energizable functionality of the Ophthalmic Lens in some embodiments. In others, the event coloration mechanism may be passive but may interact and interface with the electrical components of the Ophthalmic Lens, such as, for example, those included within the Media Insert. Event coloration mechanisms may be combined with additional functionalities that may be included in an energizable Ophthalmic Lens.

The invention claimed is:

1. An ophthalmic lens, comprising:
a soft lens portion comprising a polymerized reactive monomer mixture; and
a media insert in contact with the soft lens portion, the media insert comprising an event coloration mechanism configured to provide a visual indication in the ophthalmic lens based on an occurrence of a predefined event, wherein the event coloration mechanism comprises:
a power source;
a coloration portion electrically connected to the power source by a conductive trace; and
a tube portion comprising a body and an encapsulant layer capable of surrounding the body, the tube portion being in circuit with the conductive trace, the coloration portion, and the power source and being capable of limiting an activation of the coloration portion.

2. The ophthalmic lens of claim 1, wherein the event coloration mechanism is located within the media insert, and wherein the predefined event comprises a condition of a component located within the media insert.

3. The ophthalmic lens of claim 2, wherein the component comprises the power source and wherein the condition comprises a leeching of a caustic substance from a pre-designated area for the power source.

4. The ophthalmic lens of claim 2, wherein the predefined event comprises a predefined pH level within the media insert.

5. The ophthalmic lens of claim 2, wherein the media insert further comprises:
a variable optic element capable of altering an optical power of the ophthalmic lens in electrical communication with a processor and the power source.

6. The ophthalmic lens of claim 1, wherein the coloration portion comprises:
a liquid crystal, wherein the liquid crystal is capable of a resting orientation and a first energized orientation, and wherein the liquid crystal in the resting orientation comprises a first color and the liquid crystal in the first energized orientation comprises a second color.

7. The ophthalmic lens of claim 6, wherein the body comprises a reactive material capable of reacting with a specified tear fluid constituent, and wherein the specified tear fluid constituent is capable of permeating the encapsulant layer.

8. The ophthalmic lens of claim 1, wherein the predefined event comprises a pathogen level in tear fluid.

9. The ophthalmic lens of claim 1, wherein the predefined event comprises a biomarker level in tear fluid.

10. The ophthalmic lens of claim 1, the predefined event comprises an active agent level in tear fluid.

11. An ophthalmic lens, comprising:
a soft lens portion comprising a polymerized reactive monomer mixture; and
a media insert in contact with the soft lens portion, the media insert comprising an event coloration mechanism configured to provide a visual indication in the ophthalmic lens based on an occurrence of a predefined event;
wherein the media insert comprises:
a power source located within the media insert; and
a processor in electrical communication with the power source, and wherein the event coloration mechanism comprises:
an illumination device configured to provide illumination, in electrical communication with the power source and the processor, and
a network of optical fibers configured to be illuminated by the illumination device.

12. The ophthalmic lens of claim 11, wherein the media insert further comprises a variable optic element capable of altering an optical power of the ophthalmic lens in electrical communication with the processor and the power source.

13. The ophthalmic lens of claim 11, wherein the event coloration mechanism is located within the media insert, and wherein the predefined event comprises a condition of a component located within the media insert.

14. The ophthalmic lens of claim 13, wherein the component comprises the power source and wherein the condition comprises a leeching of a caustic substance from a pre-designated area for the power source.

15. The ophthalmic lens of claim 13, wherein the predefined event comprises a predefined pH level within the media insert.

16. The ophthalmic lens of claim 11, wherein the predefined event comprises a pathogen level in tear fluid.

17. The ophthalmic lens of claim 11, wherein the predefined event comprises a biomarker level in tear fluid.

18. The ophthalmic lens of claim 11, the predefined event comprises an active agent level in tear fluid.

19. The ophthalmic lens of claim 11, wherein the network of optical fibers are arranged in a sunburst design.

20. The ophthalmic lens of claim 11, wherein the network of optical fibers comprises a portion within an optic zone, wherein the portion within the optic zone is visible to a wearer.

21. The ophthalmic lens of claim 11, wherein:
the event coloration mechanism further comprises a first resistance tab in electrical communication with a processor, wherein the first resistance tab is configured to bind a tear fluid constituent that is indicative of the occurrence of the predefined event, wherein the binding is capable of increasing a resistance of the first resistance tab; and the processor further comprises an executable software capable of controlling the event coloration mechanism based on the resistance.

* * * * *